US012755883B2

(12) United States Patent
Tyagi

(10) Patent No.: US 12,755,883 B2
(45) Date of Patent: Oct. 6, 2026

(54) MAGNETIC TUNNEL JUNCTION BASED MOLECULAR SPINTRONICS DEVICE AND MAGNETIC RESONANCE SENSORS

(71) Applicant: University of the District of Columbia, Washington, DC (US)

(72) Inventor: Pawan Tyagi, Derwood, MD (US)

(73) Assignee: University of the District of Columbia, Washington, DC (US)

( * ) Notice: Subject to any disclaimer, the term of this patent is extended or adjusted under 35 U.S.C. 154(b) by 1129 days.

(21) Appl. No.: 17/742,775

(22) Filed: May 12, 2022

(65) Prior Publication Data

US 2022/0364189 A1 Nov. 17, 2022

Related U.S. Application Data

(60) Provisional application No. 63/187,456, filed on May 12, 2021.

(51) Int. Cl.

| | |
|---|---|
| ***H01F 10/32*** | (2006.01) |
| ***C12Q 1/70*** | (2006.01) |
| ***G01N 33/569*** | (2006.01) |

(52) U.S. Cl.

CPC ... *H01F 10/3254* (2013.01); *G01N 33/56983* (2013.01); *C12Q 1/70* (2013.01); *H01F 10/3259* (2013.01); *H01F 10/3268* (2013.01)

(58) Field of Classification Search

None

See application file for complete search history.

(56) References Cited

U.S. PATENT DOCUMENTS

| | | | | |
|---|---|---|---|---|
| 6,778,853 | B1 * | 8/2004 | Heller | A61M 37/00 604/20 |
| 11,677,131 | B1 * | 6/2023 | Carter | H01P 11/003 333/204 |
| 12,002,605 | B1 * | 6/2024 | Zhang | B82Y 10/00 |
| 2014/0113386 | A1 * | 4/2014 | Gyarfas | C12Q 1/6869 430/318 |
| 2021/0111274 | A1 * | 4/2021 | Tyagi | G01N 27/3276 |

OTHER PUBLICATIONS

Pang et al., Fixed-Gap Tunnel Junction for Reading DNA Nucleotides, 2014, ACSNANO, vol. 8, No. 12, p. 11994-12003. (Year: 2014).*

Tyagi, Spin Photovoltaic Effect on Molecule Coupled Ferromagnetic Films of a Magnetic Tunnel Junction, 2013, ASME, p. 1-7. (Year: 2013).*

* cited by examiner

*Primary Examiner* — Lore R Jarrett

(74) *Attorney, Agent, or Firm* — Whiteford, Taylor & Preston, LLP; Peter J. Davis

(57) ABSTRACT

A detection method and sensors are provided for the rapid detection of chemicals, biological and non-biological, and a wide range of viruses using magnetic tunnel junction-based molecular spintronics devices (MTJMSD) that produce unique magnetic resonance signals before and after interacting with target chemical, biochemical, viral, and other molecular agents.

19 Claims, 9 Drawing Sheets

MAGNETIC TUNNEL JUNCTION BASED MOLECULAR SPINTRONICS DEVICE AND MAGNETIC RESONANCE SENSORS

CROSS-REFERENCE TO RELATED APPLICATIONS

This application claims priority to U.S. Provisional Patent Application No. 63/187,456 entitled "Magnetic Tunnel Junction Based Molecular Spintronics Device and Magnetic Resonance Sensors for Chemical, Biological, and Viral Agents" and filed May 12, 2021. The contents of the above-identified previously filed application are incorporated herein by reference in their entireties.

STATEMENT REGARDING FEDERALLY SPONSORED RESEARCH

This invention was made with government support under contract number HRD-1914751 by the National Science Foundation, CREST Award, and under contract number NA0003945 by the U.S. Department of Energy National Nuclear Security Administration. The government has certain rights in the invention.

FIELD OF THE INVENTION

This invention is directed to the detection of chemical, biological, viral, and non-biological agents and sensors configured for the detection of such agents.

BACKGROUND

Detection of chemical, biological and non-biological molecules and agents is exceptionally critical in understanding the cause of any health or environmental problem. Detection of chemicals during the treatment or remediation process is even more critical in ensuring the success of a solution to a health or environmental issue. For example, studying the range of neurochemicals like dopamine, serotonin, glutamate, etc., is critical for the fundamental understanding of the brain and the connection between brain functioning and human health conditions. Sensors capable of carrying out such detection can enable life-saving interventions to be implemented for army or defense personnel in the frontline who experience brain injuries. Brain injuries trigger the release of several chemicals that can suggest the impact level of brain injury, and that may also be used during the treatment process. Complex chemicals, such as viruses like HIV, SARS, and CORONA-19, can present significant risks to the survivability of the whole human race. There has been a large body of research that has led to various detection methods listed in prior literature. Unfortunately, there remains a significant need for sensors capable of detecting multiple chemicals with high selectivity and accuracy. While various systems and methods of chemical detection have previously been implemented, the need for a highly compact and economical solution for chemical detection remains one of the most demanding challenges.

The utilization of the magnetic resonance property has been explored in the field of chemical and biochemical detection. Interestingly, micro-nano fabrication methods have allowed the fabrication of chemical responsive materials in the form of a chip. Such chips contain radio frequency (RF) waveguides that register a change in magnetic resonance as thin-film sensing elements interact with the analyte (Hydrogen sensor). The electron spin resonance method has been utilized to sense free radicals and several chemical analytes that possess unpaired electrons. A new branch of chemical detection is viable when an analyte with or without unpaired spin can interact with the magnetic material or integrated assembly of pattern-able magnetic materials and molecular sensors.

SUMMARY OF THE INVENTION

In accordance with certain aspects of an embodiment, provided herein is a detection method and sensors for the rapid detection of chemicals, biological and non-biological, and a wide range of viruses with unprecedented high specificity and sensitivity. Such detection method and sensors focus on using magnetic tunnel junction-based molecular spintronics devices (MTJMSD) that produce unique magnetic resonance signals before and after interacting with target chemical, biochemical, viral, and other molecular agents.

Saliva, blood, and mucus from a patient may contain the biomolecules of interest. The utility of a MTJMSD configured as described herein can be illustrated by way of example and may employ an innovative nanoscale spintronics-based portable brain chemical detection system. Brain injuries are a major cause of defense personnel losing their lives or living with a challenging disability. Sensing biochemicals that are released after the brain injury occurs may inform about the severity of brain injury and may help provide the required attention to deal with the injury. However, most previously known brain imaging or injury-specific chemical detection systems are too bulky and may not be carried in the war field. Thus, described herein are magnetic tunnel junction-based molecular spintronics sensors (FIG. 1*a*) that can specifically interact with proteins and radicals generated because of brain injury.

Still other aspects, features and advantages of the invention are readily apparent from the following detailed description, simply by illustrating several particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings, in which like reference numerals refer to similar elements, and in which:

FIG. 1(*b*) is a top-view illustration of a sensor according to certain aspects of an embodiment of the invention.

FIG. 1(*c*) is a top-view illustration of a sensor according to certain aspects of an embodiment of the invention with a drop of blood on the sensor.

FIG. 1(*d*) is a side-view illustration of a sensor according to certain aspects of an embodiment of the invention with a drop of blood containing one or more target biomolecules on the sensor that will interact with the molecular sensor to produce a change in RF signal.

FIG. 2(*b*) is a side-view illustration of a sensor according to certain aspects of an embodiment of the invention, including multilayer multiple MTIMSDs hosting multiple molecular sensors.

FIG. 2(*c*) is a side-view illustration of a sensor according to certain aspects of an embodiment of the invention, including multilayer multiple MTIMSDs hosting multiple molecular sensors, with a drop of fluid containing two or more target biomolecules on the sensor, wherein each molecular sensor interacts with a specific target biomolecule to produce unique resonance signatures.

FIG. 3(*b*) is a side-view illustration of a sensor according to certain aspects of an embodiment of the invention, including one or more virus receptors on top of a double MTJMSD.

FIG. 3(*c*) is a side-view illustration of a sensor in FIG. 3(*b*) with viruses and analytes detected.

FIG. 4(*b*) is a perspective-view illustration of the sensor in FIG. 4(*a*), further comprising virus receptors and multiple molecular sensors.

FIG. 4(*c*) is an illustration indicating that the sensor in FIG. 4(*b*) can detect multiple viruses and analytes.

FIG. 5(*b*) is a top-view illustration of the chip in FIG. 5(*a*) in contact with a drop of fluid containing analytes.

FIG. 5(*c*) is a top-view illustration of the chip in FIG. 5(*a*) submerged in a fluid containing analytes.

FIG. 5(*d*) is a side-view illustration of a sensor according to certain aspects of an embodiment of the invention, including one or more virus detectors on the sides of the MTJMSD.

FIG. 5(*e*) is a side-view illustration of the sensor in FIG. 5(*d*) in contact with fluid containing one or more viruses, whereby the virus detectors on an upper layer and the virus detectors on a lower layer contact a virus.

FIG. 5(*f*) is a graph indicating a hypothetical ESR spectra for a MTJMSD array before contacting a virus.

FIG. 5(*g*) is a graph indicating a hypothetical ESR spectra for a MTJMSD array after contacting a virus.

FIG. 6(*b*) is a side-view illustration of the MTJ array of FIG. 6(*a*) in contact with a target virus.

FIG. 7(*b*) is a side-view illustration of the sensor of FIG. 7(*a*) in contact with a target virus, forming a virus bridge.

FIG. 8(*b*) is a side-view illustration of the sensor of FIG. 8(*a*) in contact with a target virus, forming a virus bridge.

DETAILED DESCRIPTION OF THE PREFERRED EMBODIMENTS

Figure 1A:
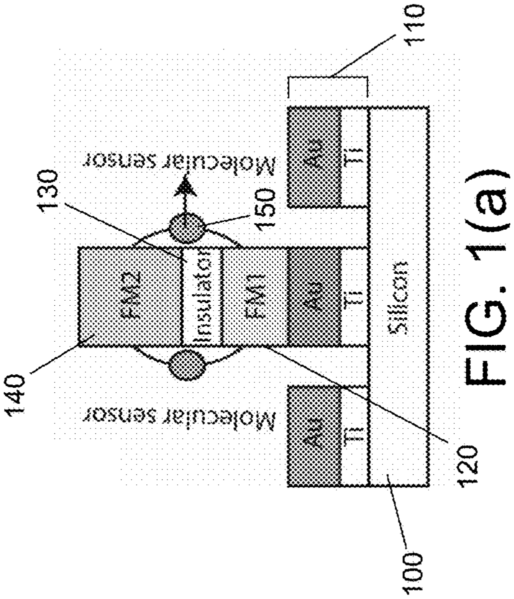
FIG. 1(*a*) is a side-view illustration of a sensor according to certain aspects of an embodiment of the invention.

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art.

Descriptions of well-known functions and structures are omitted to enhance clarity and conciseness. The terminology used herein is for the purpose of describing particular embodiments only and is not intended to be limiting of the present disclosure. As used herein, the singular forms "a," "an" and "the" are intended to include the plural forms as well, unless the context clearly indicates otherwise. Furthermore, the use of the terms a, an, etc. does not denote a limitation of quantity, but rather denotes the presence of at least one of the referenced items.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Provided according to certain aspects of an embodiment of the invention is a magnetic tunnel junction-based molecular spintronics device (MTJMSD).

Prior MTJMSD research has focused on computer technology and requires the monitoring of conductivity. However, an MTJMSD designed to interact with targeted chemicals and viruses leading to a unique magnetic resonance property can produce novel forms of highly compact, portable, specific sensors. The molecule sensor of the MTJMSD can be designed to respond to the target analyte by latching onto it by the lock and key mechanism. Under the lock and key mechanism, the molecular sensor on MTJMSD structure will be only designed to interact with specific molecules of interest, as a key only opens the lock to which it belongs.

The disclosed method focuses on the rapid detection of chemicals, biological and non-biological, and a wide range of viruses with unprecedented high specificity and sensitivity. This invention focuses on using magnetic tunnel junction-based molecular devices (MTJMSD) that produce unique magnetic resonance signals before and after interacting with target chemicals and viruses.

Referring to FIGS. 1-4, 5(*a*)-(*e*), and 6-8, in some embodiments of the invention, MTJMSDs are made up of ferromagnetic layers 120/140 (FM) that are coupled by the molecular channel 150 (FIG. 1*a*). Molecular channels 150 dominate the coupling between the top FM layer 140 (FM2) and the bottom FM layer 120 (FM1) compared to the inert and robust insulating barrier 130 placed between FM1 and FM2. The molecular channel 150 is designed to serve as a molecular sensor to detect the analytes or chemicals (FIG. 1 *a*). MTJMSD can be patterned on a waveguide and plugged into a magnetic resonance instrument (FIG. 1*b*), analogous to a popular in-home glucose meter system that utilizes a sensor strip for a blood sample and compact glucose meter. A magnetic resonance device supplies radio frequency (RF) signals 200 and required a magnetic field to detect any changes in the incoming RF signal 200 (RF in) due to the interaction of the MTJMSD with chemical analytes (FIG. 1*b-c*). The comparison between RF-in 200 and RF out 210 identifies the types and quantity of the analyte (FIG. 1*d*). The molecular sensor 150 interacts with the target chemical by way of a lock and key mechanism (FIG. 1*d*). Only the target chemical will be able to produce a response.

Still referring to FIGS. 1-4, 5(*a*)-(*e*), and 6-8, the device includes a substrate 100 and a ferromagnetic structure appended to an upper surface of the substrate, the ferromagnetic structure comprising a ground layer on the substrate 110, a first ferromagnetic layer 120 on the ground layer 110, a first insulator layer 130 on the first ferromagnetic layer 120, a second ferromagnetic layer 140 on the first insulator layer 130, and a material comprising at least one virus receptor 158/160/700/710 or molecular sensor 150/151/155/156. In accordance with certain aspects of an embodiment of the invention, the device may comprise one ferromagnetic structure. In accordance with certain aspects of an embodiment of the invention, the device may comprise two or more ferromagnetic structures, and each ferromagnetic structure may have a side that is perpendicular to at least one ferromagnetic layer, wherein the side of one ferromagnetic structure and the side of another ferromagnetic structure form a gap. In accordance with certain aspects of an embodiment of the invention, the gap has a width, as measured by the closest point between the two sides, of about 1 nm to 1000 nm.

Still referring to FIGS. 1-4, 5(*a*)-(*e*), and 6-8, in accordance with certain aspects of an embodiment of the invention, the substrate 100 may be formed from any suitable material, such as silicon, silicon dioxide, gallium arsenide, silicon nitride, glass, and any suitable combination thereof. The substrate may be any thickness suitable for its use, including a thickness of 200 μm to 5000 μm. The substrate 100 may be formed by any process known in the art, including typical processes used in the semiconductor industries.

Still referring to FIGS. 1-4, 5(*a*)-(*e*), and 6-8, in accordance with certain aspects of an embodiment of the invention, the ground layer 110 may be formed from any suitable material, such as titanium, gold, tantalum, chromium, aluminum, and any suitable combination thereof. The ground layer 110 may be any thickness suitable for its use, including a thickness of 10 nm to 200 nm. The ground layer 110 may be appended to the substrate 100 by any process known in the art, including sputtering deposition, thermal evaporation, and E-beam deposition.

Still referring to FIGS. 1-4, 5(*a*)-(*e*), and 6-8, in accordance with certain aspects of an embodiment of the invention, the first ferromagnetic layer 120 may be formed from any suitable material, such as nickel, iron, and cobalt, and any suitable combination thereof. The first ferromagnetic layer 120 may be any thickness suitable for its use, including a thickness of 1 nm to 100 nm. The first ferromagnetic layer 120 may be appended to the ground layer 110 by any process known in the art, including sputtering deposition, thermal evaporation, and E-beam deposition.

Still referring to FIGS. 1-4, 5(*a*)-(*e*), and 6-8, in accordance with certain aspects of an embodiment of the invention, the first insulator layer 130 may be formed from any suitable material, such as aluminum oxide, magnesium oxide, silicon dioxide, titanium dioxide, boron nitride, and any suitable combination thereof. The first insulator layer 130 may be any thickness suitable for its use, including a thickness of 0.5 nm to 1000 nm. The first insulator layer 130 may be appended to the first ferromagnetic layer 120 by any process known in the art, including sputtering deposition, thermal evaporation, chemical vapor deposition, atomic layer deposition, and E-beam deposition.

Still referring to FIGS. 1-4, 5(*a*)-(*e*), and 6-8, in accordance with certain aspects of an embodiment of the invention, the second ferromagnetic layer 140 may be formed from any suitable material, such as nickel, iron, and cobalt, and any suitable combination thereof. The second ferromagnetic layer 140 may be any thickness suitable for its use, including a thickness of 1 nm to 100 nm. The second ferromagnetic layer 140 may be appended to the first insulator layer 130 by any process known in the art, including sputtering deposition, thermal evaporation, and E-beam deposition.

Still referring to FIGS. 1-4, 5(*a*)-(*e*), and 6-8, in accordance with certain aspects of an embodiment of the invention, the molecular channel 150 may be formed from any suitable material, such as DNA, single molecule magnet (SMM), organometallic molecules, porphyrin, polymeric chains, and any suitable combination thereof. The molecular channel 150 may be any thickness suitable for its use, including a thickness of 1 nm to 1200 nm and may be any length suitable for its use, such that the molecular channel is attached to the first ferromagnetic layer 120 and the second ferromagnetic layer 140. The molecular channel 150 may be attached to the first ferromagnetic layer 120 and the second ferromagnetic layer 140 by any process known in the art, including self-assembly and electrodeposition. The molecular channel may be attached on the side of the ferromagnetic structure, the top of the ferromagnetic structure, and any combination thereof.

Figure 4B:
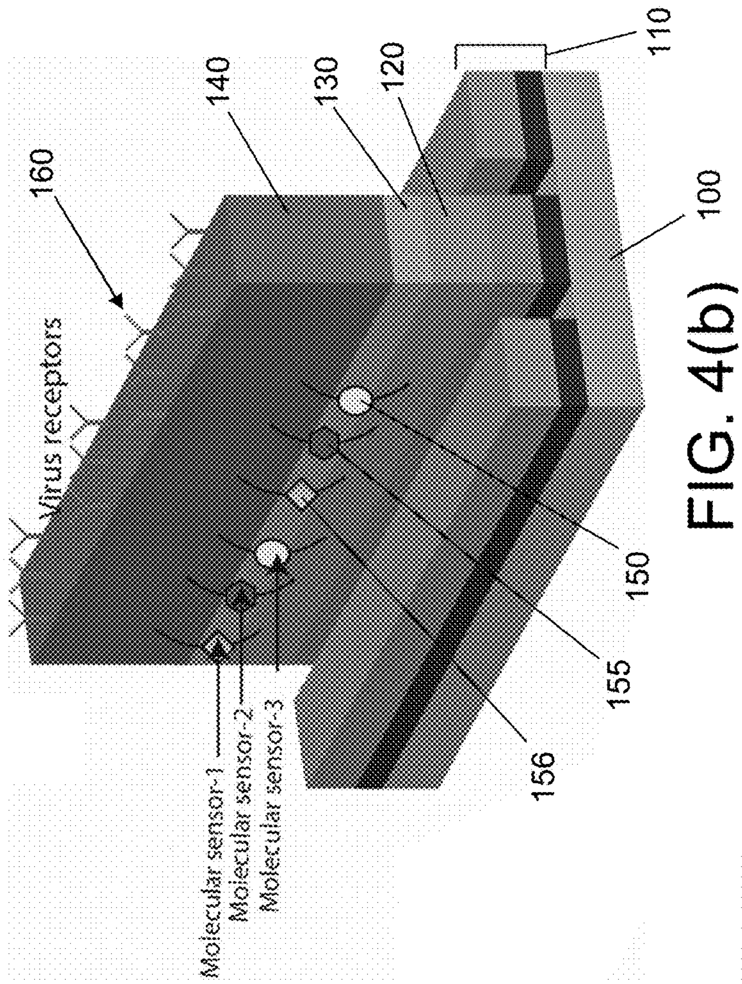
FIG. 4(*a*) is a side-view illustration of a sensor according to certain aspects of an embodiment of the invention, including a wave form MTJMSD.
Figure 4A:
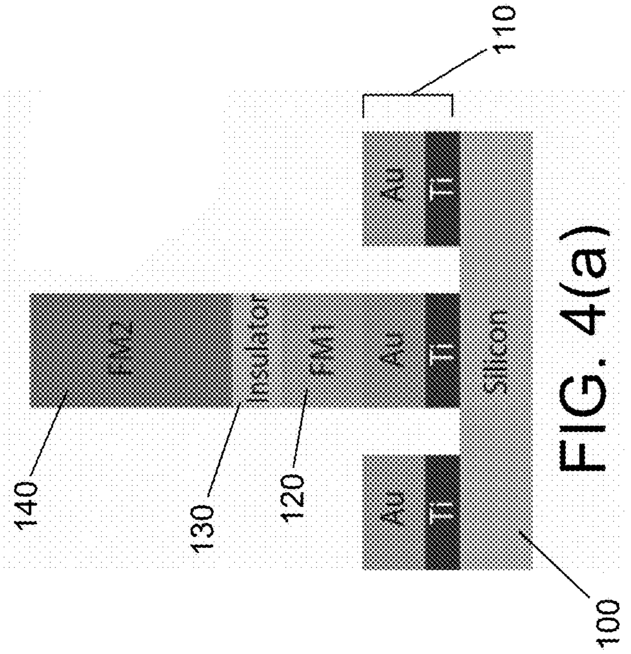

Now referring to FIGS. 4(*b*), the molecular channel 150 may comprise more than one molecular channel 155/156 such that two or more analytes can be detected in a single sample.

Now referring to FIGS. 2 and 3, and in accordance with certain aspects of an embodiment of the invention, the device may further comprise a second insulator layer 131, a third ferromagnetic layer 141, and, optionally, a molecular channel 151 attaching the second ferromagnetic layer 140 to the third ferromagnetic layer 141.

Still referring to FIGS. 2 and 3, in accordance with certain aspects of an embodiment of the invention, the second insulator layer 131 may be formed from any suitable material, such as aluminum oxide, magnesium oxide, silicon dioxide, titanium dioxide, boron nitride, and any suitable combination thereof. The second insulator layer 131 may be any thickness suitable for its use, including a thickness of 0.5 nm to 1000 nm. The second insulator layer 131 may be appended to the second ferromagnetic layer 140 by any process known in the art, including sputtering deposition, thermal evaporation, chemical vapor deposition, atomic layer deposition, and E-beam deposition.

Still referring to FIGS. 2 and 3, in accordance with certain aspects of an embodiment of the invention, the third ferromagnetic layer 141 may be formed from any suitable material, such as nickel, iron, and cobalt, and any suitable combination thereof. The third ferromagnetic layer 141 may be any thickness suitable for its use, including a thickness of 1 nm to 100 nm. The third ferromagnetic layer 141 may be appended to the second insulator layer 131 by any process known in the art, including sputtering deposition, thermal evaporation, and E-beam deposition.

Still referring to FIGS. 2 and 3, in accordance with certain aspects of an embodiment of the invention, the molecular channel 151 may be formed from any suitable material, such as single molecule magnet, porphyrin, polymeric chains, DNA, and any suitable combination thereof. The molecular channel 151 may be any thickness suitable for its use, including a thickness of 1 nm to 1200 nm and may be any length suitable for its use, such that the molecular channel is attached to the second ferromagnetic layer 140 and the third ferromagnetic layer 141. The molecular channel 151 may be attached to the second ferromagnetic layer 140 and the third ferromagnetic layer 141 by any process known in the art, including self-assembly and electrodeposition.

Now referring to FIGS. 3-8, in certain configurations, the MTJMSD may comprise virus sensors 160/700/710 in addition to, or instead of, molecular detectors 150/151. In accordance with certain aspects of an embodiment of the invention, the virus sensors 160/700/710 may be formed from any suitable material, such as enzymes and proteins, and any suitable combination thereof. In certain configurations, the virus sensor 160 may be attached to the second ferromagnetic layer 140 or the third ferromagnetic layer 141. In certain configurations, the virus sensors 700/710 may be attached to two or more ferromagnetic layers, such as by attaching one virus sensor 700 to the first ferromagnetic layer 120 and attaching another virus sensor 710 to the second ferromagnetic layer 140. Where virus sensors 700/710 are attached to two or more ferromagnetic layers, such as the first ferromagnetic layer 120 and the second ferromagnetic layer 140, a target virus may interact with a first virus sensor 700 and a second virus sensor 710 to form a virus bridge between two ferromagnetic layers. In accordance with certain aspects of an embodiment of the invention, a virus sensor 160 on one ferromagnetic structure has a distance of about 10 nm to 1000 nm from a virus sensor 160 on another ferromagnetic structure.

In certain configurations, the device may be provided in a system with a magnetic resonance device that supplies radio frequency signals and a magnetic field detector, and optionally a fluid. The fluid may comprise any air or liquid to be tested. In certain configurations, a sample of air is exposed to a liquid, and then that liquid may be tested using the device.

The device may be utilized in any suitable application, such as in a laboratory, in a handheld unit, in a drone or similar aerial or other mobile platform, or in such other related applications as will readily occur to those skilled in the art.

Provided herein are non-limiting exemplary implementations according to certain aspects of embodiments of the invention described above.

Figure 1B:
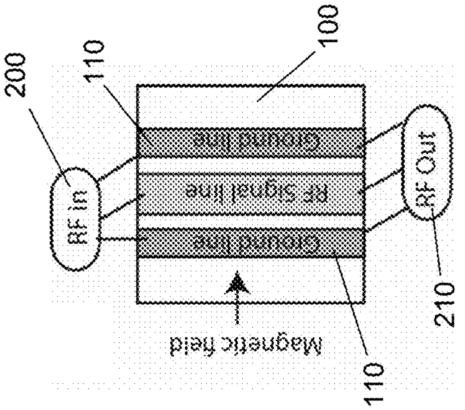
Figure 1C:
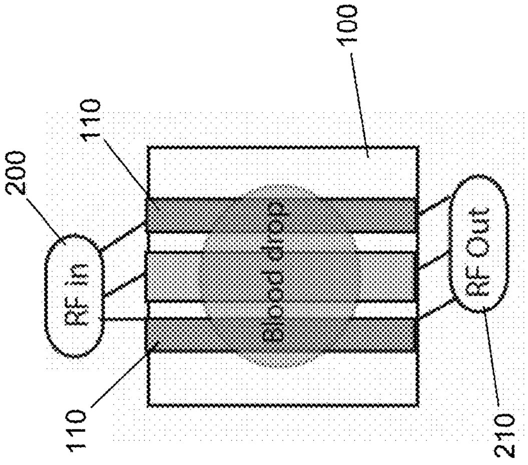
Figure 1D:
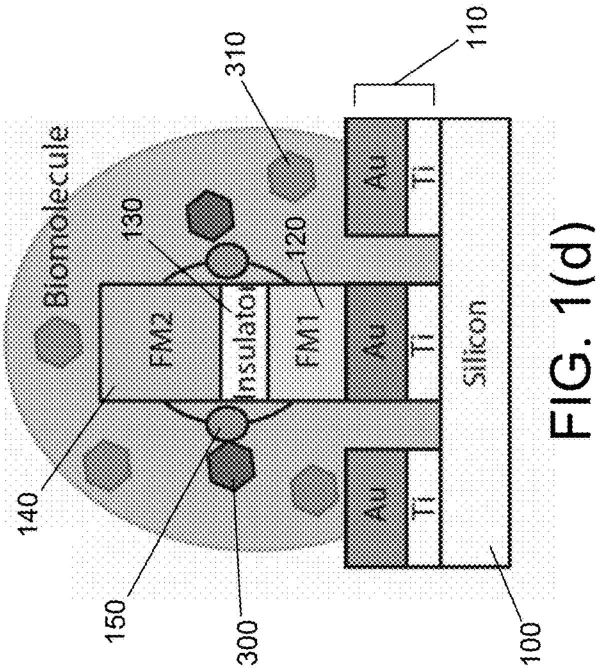

Example 1, Waveguide form MTJMSD for analyte detection in fluid: A proposed sensor may be in the form of a chip (FIG. 1B) on which a blood drop can be placed (FIG. 1*c*), such as a blood glucose sensor. Analytes 300, such as biochemicals known to cause brain injury, will interact with the molecular channel 150 utilized in the proposed sensor (FIG. 1*d*). Also, for the simultaneous detection of multiple chemicals, the magnetic materials FM2 140 and FM1 120 used in the sensor can also be functionalized, and hence there will be multiple sensing units. This chip may be inserted into a portable magnetic resonance unit to detect the change in response due to the interaction between targeted biochemicals and sensing units on the nanoscale spintronics devices. The sensing is done by nanoscale elements in the sensor, and a very small, expectedly nanomolar concentration of biochemicals can be detected with high specificity. The sensing operation will be based on the change in RF signal running through the molecular spintronics device, and that change is shown in FIG. 5(*f*), which shows a non-limiting exemplary signal prior to interaction with a target analyte, and FIG. 5(*g*), which shows a non-limiting exemplary signal after interaction with a target analyte. This device will produce a distinctive response in the form of a change in the microwave resonance signal. For example, each molecular spintronics device exhibits a unique resonance signal, and the signal uniqueness is directly related to the magnetic electrodes (FM1 120 and FM2 140) and molecular sensing element 150 placed along the sides of the tunnel junction (FIG. 1*a*). As a biomolecule 300 will interact with the molecular sensor 150, the change in magnetic resonance profile will be registered. The change in magnetic resonance profile will be mapped to the specific biomolecule type and concentration. The fabrication of the proposed sensor can be accomplished in a regular microfabrication process in a laboratory.

Figures 2A, 2B, 2C:
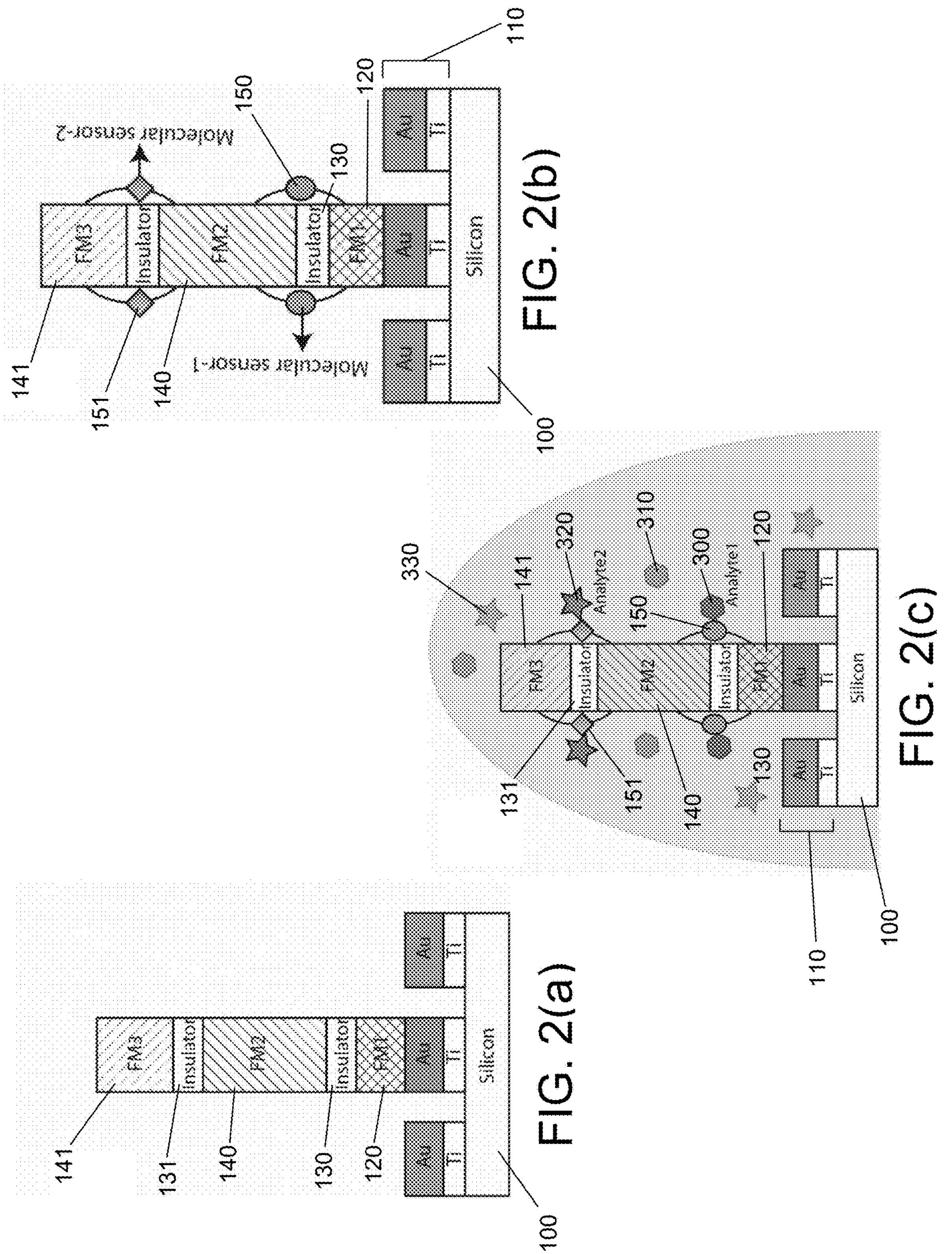
FIG. 2(*a*) is a side-view illustration of a sensor according to certain aspects of an embodiment of the invention, including multilayer multiple MTIMSDs.

Example 2, Waveguide form MTJMSD for analyte detection in fluid: MTJMSD and magnetic resonance sensors can be based on multiple magnetic tunnel junctions comprising FM-Insulator-FM units in the waveguide form (FIG. 2*a*). Multiple molecular sensors, molecular sensor-1 150 and molecular sensor-2 151 in FIG. 2*b*, can be placed in the vertical form. FM1 120 and FM2 140 can be made up of pure and alloy forms of nickel (Ni), iron (Fe), and cobalt (Co), and other materials. When a fluid containing two analytes 300/320 of interest will be placed on the MTJMSD-MR sensor, molecular sensors will react with the corresponding analyte. For example, analyte 1 300 and analyte 2 320 will only bond with molecular sensor 1 150 and molecular sensor 2 151, respectively. Each interaction between molecular sensor 150/151 and analyte 300/320 will yield the change in magnetic coupling between FM layers 120/140/141. The magnetic resonance scan will register the different signals yielded by the analyte 1 300 interaction with the molecular sensor 1 150 and analyte 2 320 interaction with the molecular sensor 2 151. The top view of the completed sensor with two molecular sensors of FIG. 2 will be the same as shown for one molecular sensor (FIG. 1B).

Figure 3A:
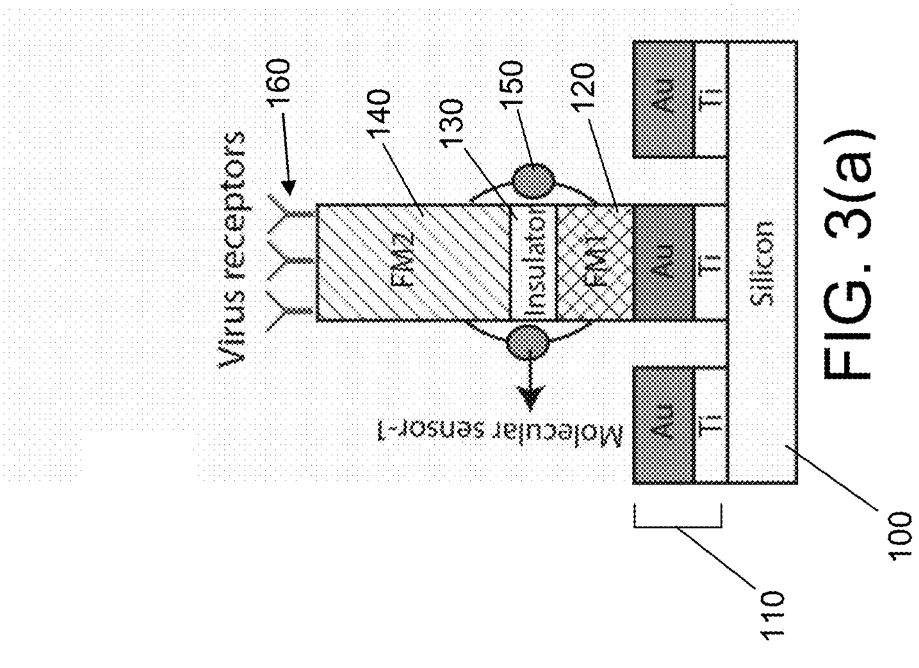
FIG. 3(*a*) is a side-view illustration of a sensor according to certain aspects of an embodiment of the invention, including one or more virus receptors on top of a single MTJMSD.
Figure 3B:
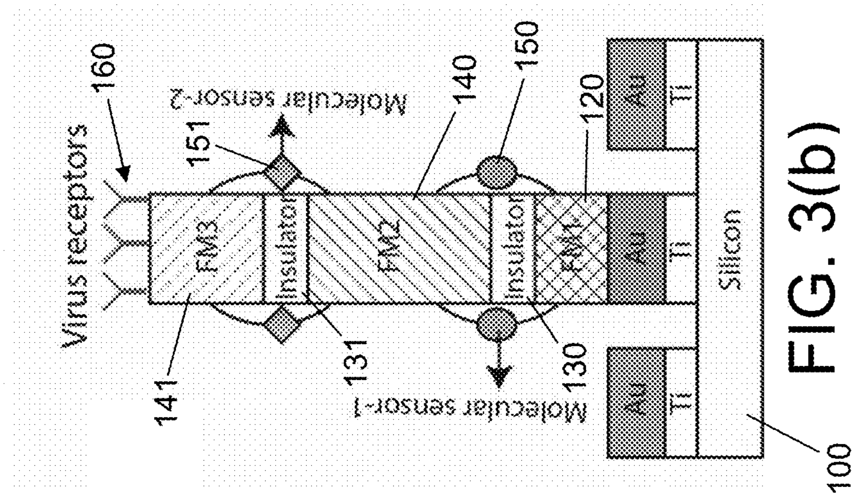
Figure 3C:
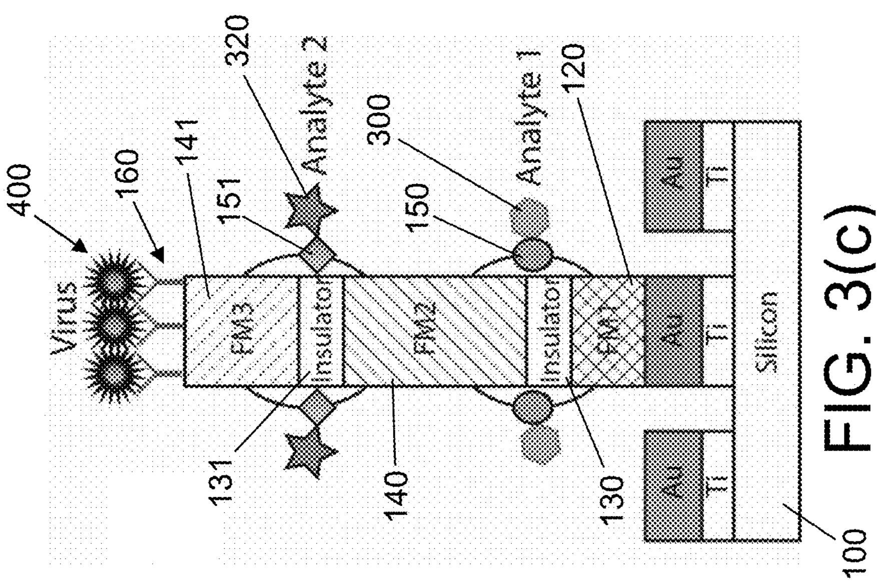

Example 3, Waveguide form MTJMSD for chemical and virus detection: An MTJMSD patterned in the waveguide form will detect virus and chemical analyte simultaneously. For this objective, the topmost ferromagnetic electrode (FIG. 3(*a*), 140; FIGS. 3(*b*)-(*c*), 141) can be functionalized with virus receptor units 160. Such virus receptors 160 can be placed on the top of a single magnetic tunnel junction (FIG. 3*a*) or on the top of multiple magnetic tunnel junctions (FIG. 3*b*) based on MTJMSDS. This method will allow the change in the magnetic resonance signal arising due to the interaction between a target virus 400 and virus receptors 160 present on the top (FIG. 3*c*). The thickness of the top FM layer (FIG. 3(*a*), 140; FIGS. 3(*b*)-(*c*), 141) will be optimized to produce a high signal-to-noise ratio, preferably at least 2:1, and more preferably at least 5:1, in the signal originating due to the interaction between the virus and ferromagnetic electrodes. The molecular sensor connected between the ferromagnetic layers along the side edges will be capable of detecting targeted analytes, as discussed above. Hence, this method allows the detection of analytes 300/320 and viruses 400 simultaneously.

Figure 4C:
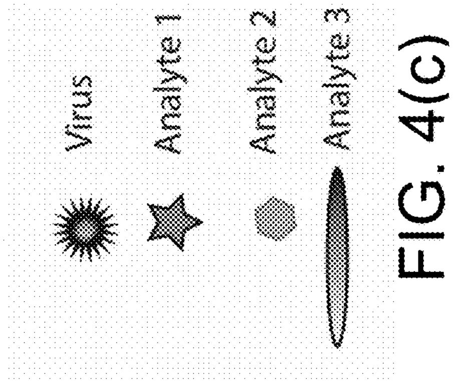

Example 4, Waveguide form MTJMSD multi-chemical and virus sensors: For simplifying the multiple analyte detections process, a single tunnel junction possessing multiple molecular sensors 150/155/156 can be used (FIG. 4). This method would enable the utilization of a single magnetic tunnel junction where multiple chemical sensors 150/155/156 will be connected between the two ferromagnets (FM1 120 and FM2 140) (FIG. 4*b*). The interaction between different molecular sensors 150/155/156 with different analytes (FIG. 4*c*) will register the unique difference in magnetic resonance in magnetic resonance spectra. The dimensions of the MTJMSD sensors can be optimized to yield a desired sensitivity range. The disclosed approach also enables the detection of viruses (or other chemicals) due to the interactions of virus receptors 160 present on the top of the top FM2 140 ferromagnet with the target virus.

Figure 5A:
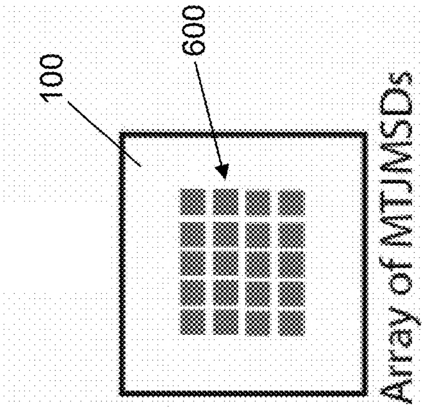
FIG. 5(*a*) is a top-view illustration of an array of MTJMSD fabricated on a chip for cavity-based Electron Spin Resonance (ESR) equipment.
Figure 5B:
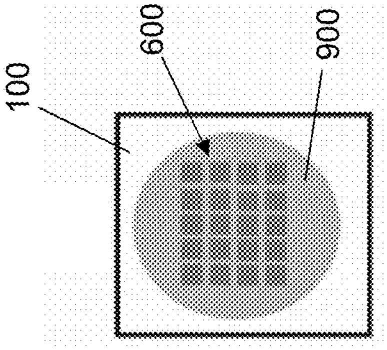

Example 5, MTJMSD chemical sensor for Cavity based Magnetic Resonance Spectrometer: MTJMSD fabrication is based on highly versatile and flexible photolithography and thin film deposition methods. MTJMSD sensors can be designed to work with a cavity-based electron spin resonance (ESR) spectrometer. For example, commercially available Brucker Magnettech ESR5000 cavity-based Electron spin resonance equipment is compact (1.5 ft×1.0 ft footprint), portable, robust, and extremely sensitive towards changes in resonance signals. Such a desktop version of the instrument can work with the disclosed MTJMSD sensors. For example, a 2 mm×4 mm chip can be mass-produced with an array of MTJMSD (FIG. 5*a*) to fit in the resonance cavity of such desktop equipment. These MTJMSD arrays can be placed on a horizontal sample carrier where fluid-carrying target sensors and viruses will be placed on the top of the sensor. A MTJMSD sensor offers unprecedented opportunity to use cavity-based benchtop electron spin resonance with great flexibility as such sensors can also be placed in a test tube along with a virus or analyte carrying medium. All of the above-mentioned waveguide form MTJMSD sensors disclosed in Examples 1-4 can be produced in the array form MTJMSD (FIG. 5*a*). Array form MTJMSD will be compatible with cavity-based signal detection in benchtop ESR instruments.

A MTJMSD sensor on the chip can be designed to target specific viruses from a liquid drop 900 (FIG. 5*b*), such as saliva, mucus, blood, cell culture media, or any other desired fluid.

Figure 5C:
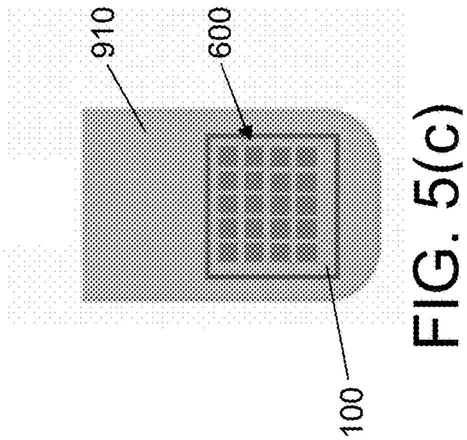
Figure 5D:
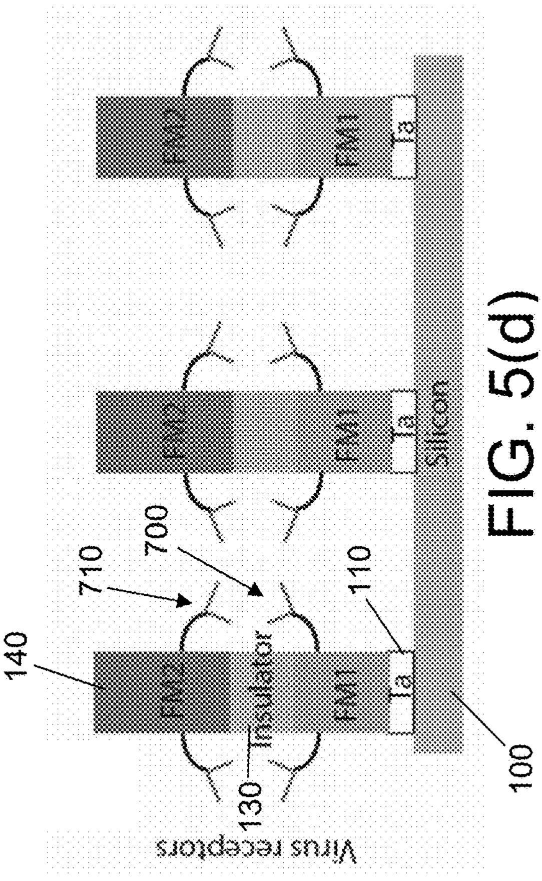
Figure 5E:
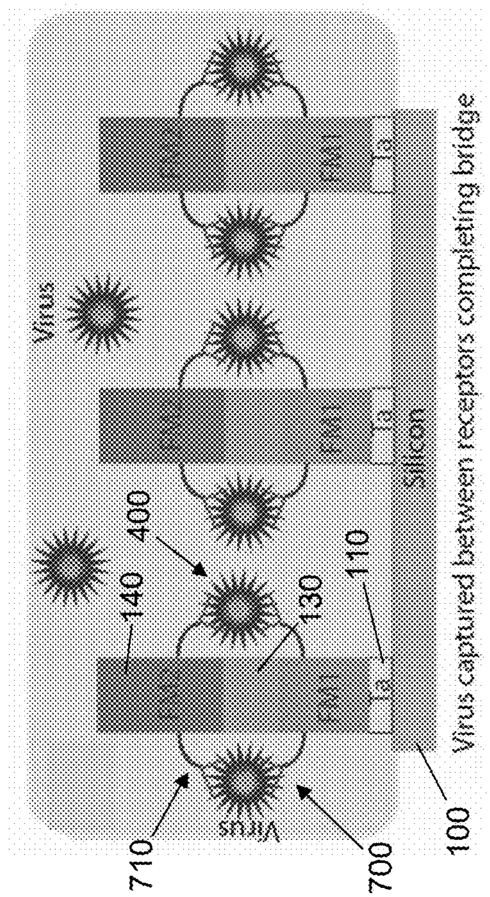
Figure 5F:
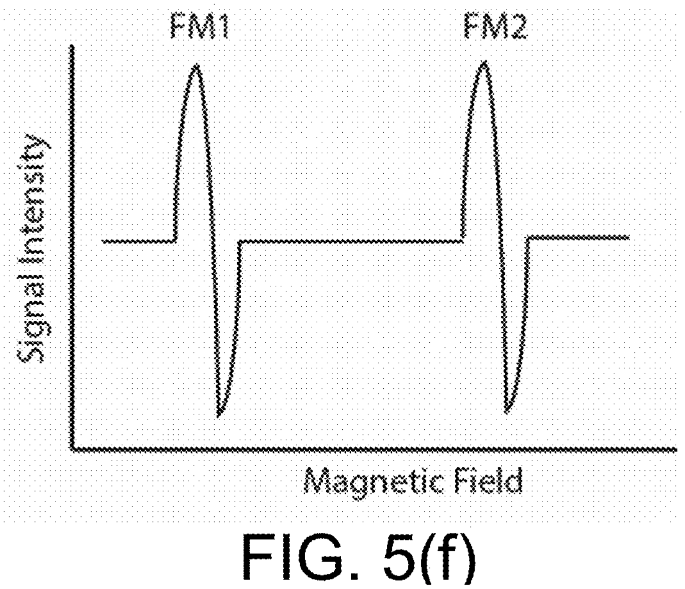
Figure 5G:
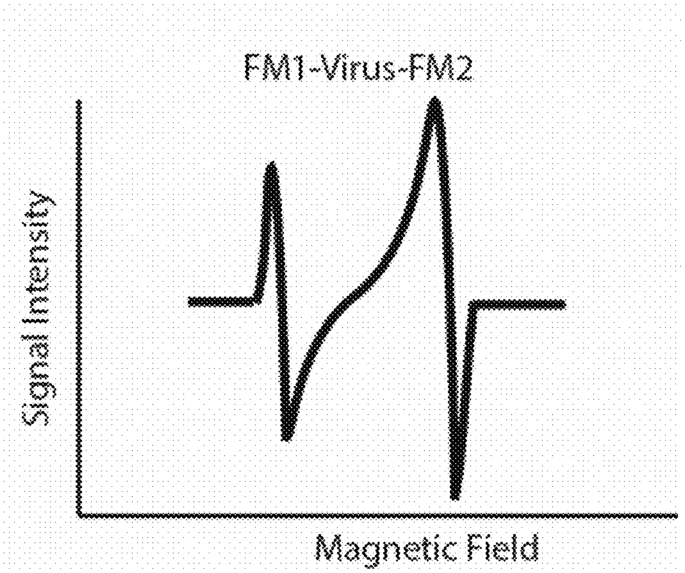

Advantageously, this 2-3 mm wide chip carrying MTJMSD array (FIG. 5*a*) can be fully submerged in a liquid medium 910 as well (FIG. 5*c*). The interaction of biomolecules, chemicals, and viruses can produce unique signatures in the ESR spectra for specific and high sensitivity detections. The chip for virus detection will possess specific receptors on both sides of the insulating spacer between FM1 120 and FM2 140 ferromagnets (FIG. 5*d*). The receptors 700/710 along the MTJMSD edges can resemble the chemistry and mechanisms of receptors found in a human and animal body. The gap between the two receptors will be governed by the thickness of the insulating spacer 130 (FIG. 5*d*). The insulating spacer 130 thickness can be optimized to target the virus 400 of specific sizes. For example, HIV and Rhinovirus will require spacer thickness to be around 30 nm. However, corona virus will require spacer thickness of up to ~100 nm. Similarly, the Ebola virus that is of ~1000 nm length will require spacer thickness of around ~1000 nm. The detection of the virus 400 will be possible as soon as a virus 400 is trapped between the two receptor links 700/710 (FIG. 5*e*). Trapping of virus 400 between receptors 700/710 will complete the additional channels of spin transport. These different channels will produce a stronger exchange coupling between two ferromagnetic electrodes of each MTJMSD. The virus 400 or analyte-induced strong exchange coupling will create an antiferromagnetic or ferromagnetic type coupling between two ferromagnetic electrodes. The hypothetical ESR spectra of MTJMSD before interaction with the virus are expected to show uncoupled signals (FIG. 5*f*). However, virus or analyte bridges along the edges will produce coupled resonance modes. Each virus or analyte is expected to produce unique ESR spectra (FIG. 5*g*). Making a library of such responses will allow the fast and accurate detection of viruses and similar analyses of interests.

Figure 6A:
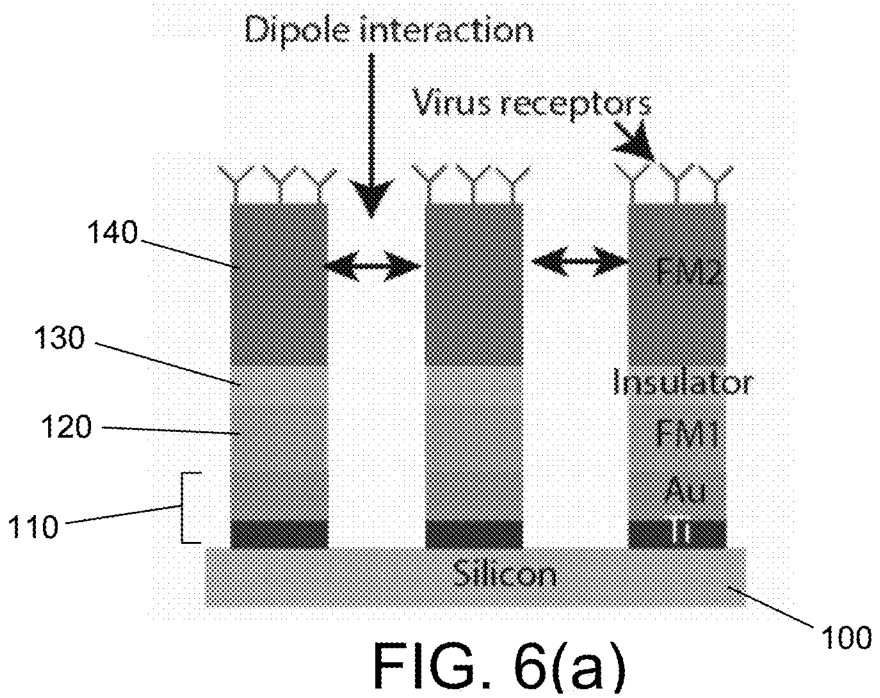
FIG. 6(*a*) is a side-view illustration of a molecular tunnel junction (MTJ) array, including virus receptors on the upper layer of the array.
Figure 6B:
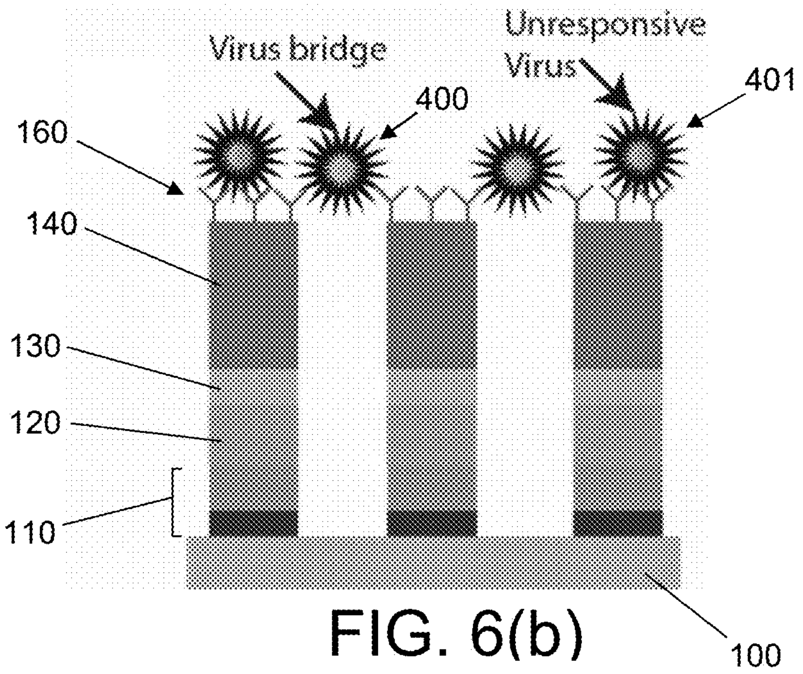

Example 6, Dipole interaction-based virus detection on Magnetic tunnel junction arrays: MTJMSD elements placed at 30-1000 nm range will interact with each other via dipolar interaction. Dipolar coupling is well established among the magnetic materials and can be easily experienced in ESR experiments. This method focuses on fabricating thousands of magnetic tunnel junctions at a separation of 20-1500 nm from each other. The MTJ array will have a virus or analyte receptor 160 on the top layer (FIG. 6*a*). As the target virus 400 will bridge the gap between the two MTJs, the strength of dipolar interaction will increase significantly (FIG. 6*b*). The ESR spectra will capture the change in dipolar interaction among the MTJs due to the virus bridge. Additionally, FM2 140 thickness can be optimized to include or avoid the effect of virus docking 401 on the FM2 140 top surface. Reducing FM2 140 thickness will allow the effect of virus or analyte interaction with the receptors 160 present on the FM2 140 top surface. Similar to the method described in FIG. 5*b*-*c*, the dipolar interaction-based sensor can function if the virus- or analyte-carrying fluid is placed in the form of a drop 900 (FIG. 5*b*) or MTJ-array chip is submerged in the fluid 910 (FIG. 5*c*).

Figure 7A:
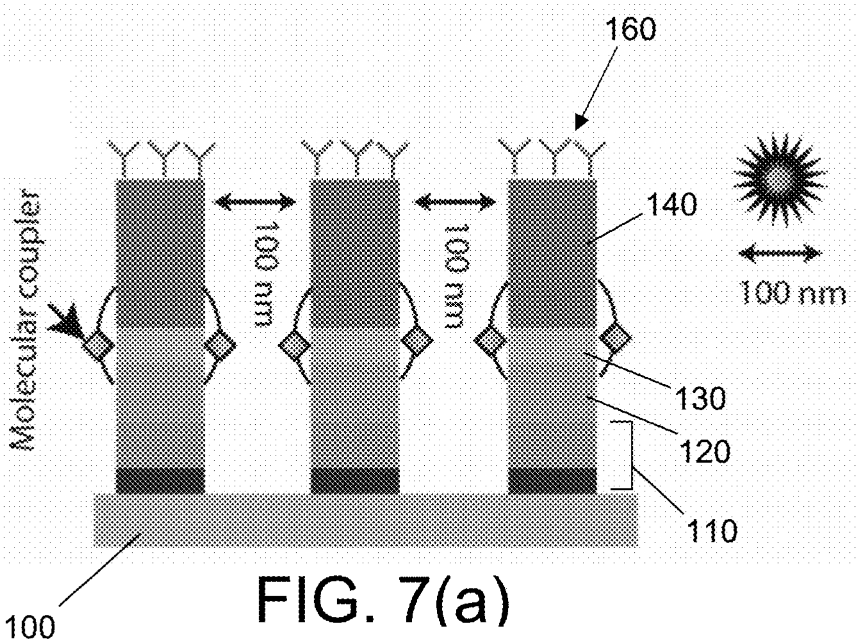
FIG. 7(*a*) is a side-view illustration of a sensor according to certain aspects of an embodiment of the invention, including one or more virus receptors on top of multiple MTJMSDs, such that the virus receptors and one or more viruses form a virus bridge between two adjacent MTJMSDs, and including molecular couplers bridging two or more layers, and the MTJMSDs are configured to produce different dipolar interactions.
Figure 7B:
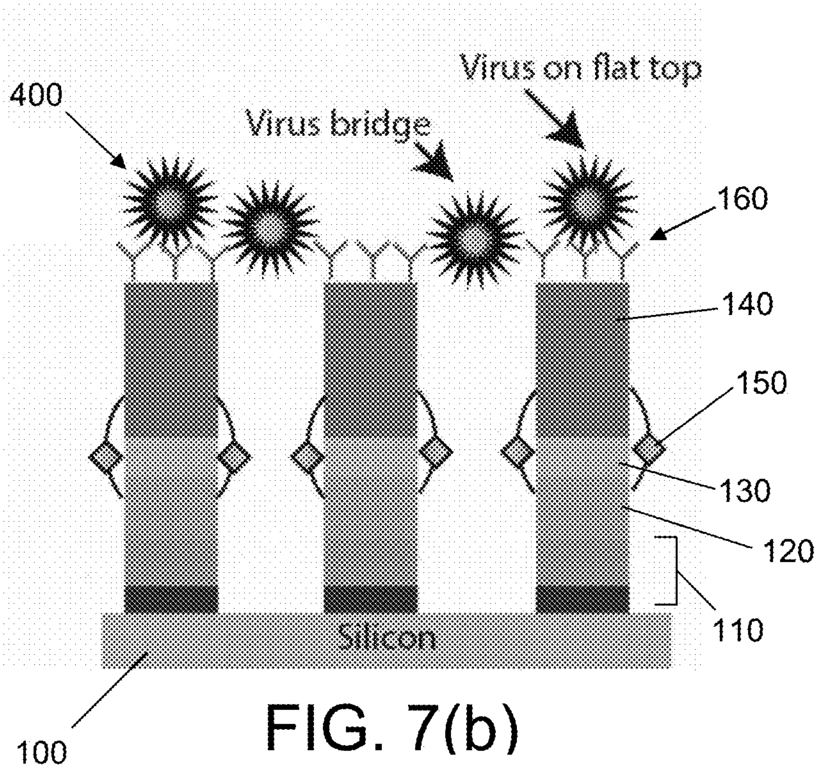

Example 7, Dipole interaction-based virus detection on MTJMSD arrays: The method of detecting viruses by way of recording change in dipolar interaction also applies to the MTJMSD array. An MTJMSD array, with a molecular sensor channel placed across the insulating spacer along the edges, with virus receptors 160 on the top can be optimally spaced from each other. For example, the detection of the Corona virus will require ~100 nm spacing between MTJMSD (FIG. 7*a*). Viruses 400 trapped between receptors 160 will bridge the gap between MTJMSD to enhance the strength of the dipolar coupling (FIG. 7*b*). Benchtop ESR can register the change in dipolar interaction. Additionally, the effect of virus docking 401 on the MTJMSD top surface can be included or avoided to strengthen the disclosed dipolar interaction-based detection. The molecular coupler between two ferromagnets (FIG. 7*a*) can be used for detecting additional or complementary analytes from the fluid.

Figure 8A:
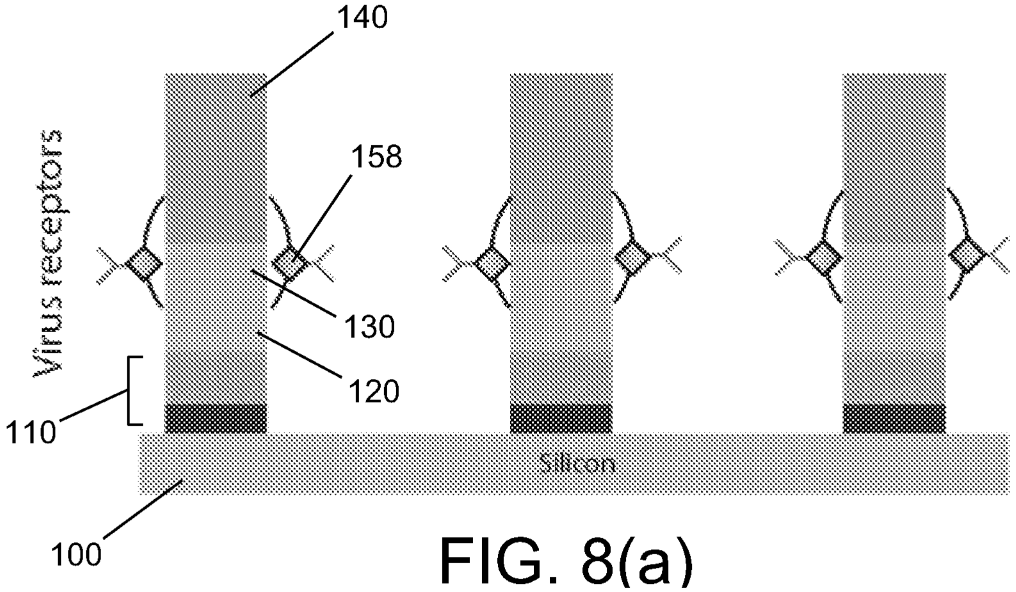
FIG. 8(*a*) is a side-view illustration of a sensor according to certain aspects of an embodiment of the invention, including molecular sensing channels that interact with target viruses and/or analytes.
Figure 8B:
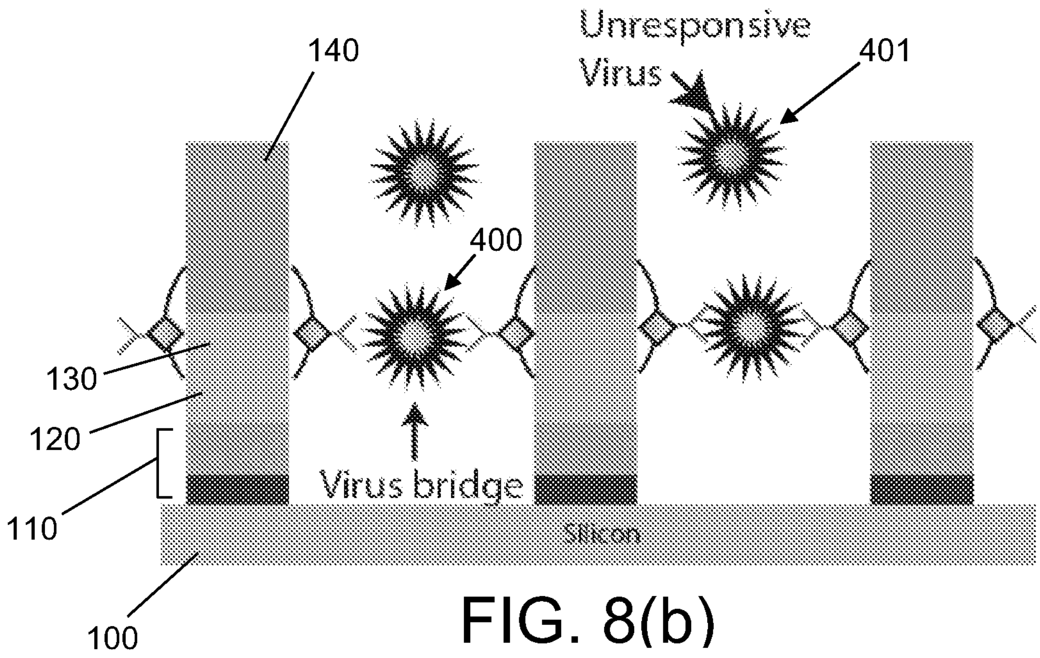

Example 8, Inter-molecular dipolar interaction-based sensing with MTJMSD array: The virus or analyte receptors 158 can be part of the molecular sensor that is bridged across insulating spacer between two ferromagnets (FIG. 8*a*). As a virus 400 will be trapped between the two receptors 158 associated with two different MTJMSD posts, the strength of dipolar interaction will increase. Anticipated ESR spectra is shown before and after the introduction of virus between two receptors (FIG. 8*b*).

What is claimed is:

1. A molecular tunnel junction based molecular spintronics device comprising:

a substrate having an upper surface;

a ferromagnetic structure appended to the top of the upper surface of the substrate and extending in a direction perpendicular to said upper surface, wherein the ferromagnetic structure comprises:

a ground layer, a first ferromagnetic layer appended to a top surface of the ground layer;

a first insulator layer appended to a top surface of the first ferromagnetic layer;

a second ferromagnetic layer appended to a top surface of the first insulator layer;

a material attached to the first ferromagnetic layer or the second ferromagnetic layer, said material selected from a virus sensor or a molecular detector, and a waveguide comprising a pair of ground lines flanking said ferromagnetic structure.

2. The device of claim 1, wherein the device comprises two or more ferromagnetic structures appended to the upper surface of the substrate and extending in a direction perpendicular to said upper surface, wherein each said ferromagnetic structure is separated from each adjacent ferromagnetic structure by a gap, wherein said two or more ferromagnetic structures form a line or a rectangular array, and wherein said pair of groundlines flank said line or opposite sides of said rectangular array.

3. The device of claim 2, wherein each said gap has a width of about 1 nm to 1000 nm.

4. The device of claim 2, wherein the material attached to said first ferromagnetic layer or said second ferromagnetic layer is a virus sensor.

5. The device of claim 2, wherein a first virus sensor is attached to one of said two or more ferromagnetic structures, and a second virus sensor is attached to a second of said two or more ferromagnetic structures and said first virus sensor and said second virus sensor are separated by a distance of about 10 nm to 1000 nm.

6. The device of claim 1, wherein the material attached to said first ferromagnetic layer or said second ferromagnetic layer is a virus sensor.

7. The device of claim 1, wherein the material attached to said first ferromagnetic layer or said second ferromagnetic layer is a molecular detector.

8. The device of claim 7, wherein the molecular detector comprises two points of attachment, wherein a first point of attachment is the first ferromagnetic layer and a second point of attachment is the second ferromagnetic layer.

9. The device of claim 1, wherein the material attached to said first ferromagnetic layer or said second ferromagnetic layer is attached to the second ferromagnetic layer, wherein the material attached to the second ferromagnetic layer is positioned on a top surface of the ferromagnetic structure.

10. The device of claim 1, further comprising:

a second insulator layer appended to a top surface of the second ferromagnetic layer; and a third ferromagnetic layer appended to a top surface of the second insulator layer.

11. The device of claim 10, wherein the material attached to said first ferromagnetic layer or said second ferromagnetic layer has at least two points of attachment, wherein a first point of attachment is the second ferromagnetic layer and a second point of attachment is the first ferromagnetic layer or the third ferromagnetic layer.

12. The device of claim 10, wherein the device comprises two or more ferromagnetic structures appended to the upper surface of the substrate and extending in a direction perpendicular to said upper surface, wherein each said ferromagnetic structure is separated from an adjacent ferromagnetic structure by a gap.

13. The device of claim 12, wherein the gap has a width of about 1 nm to 1000 nm.

14. The device of claim 10 further comprising a radio frequency signal source; a radio frequency signal detector, and a magnetic field generator.

15. The device of claim 14, further comprising a fluid in contact with the substrate and the ferromagnetic structure.

16. A method of detecting a virus, comprising:

providing the system of claim 14;

causing a radio frequency to contact the device;

generating a magnetic field;

taking a first magnetic resonance measurement;

causing the device to contact a fluid;

taking a second magnetic resonance measurement after the device is in contact with the fluid; and detecting a change in the magnetic field between the first magnetic resonance measurement and the second magnetic resonance measurement.

17. The device of claim 1 further comprising a radio frequency signal source, a radio frequency signal detector; and a magnetic field generator.

18. The device of claim 17, further comprising a fluid in contact with the substrate and the ferromagnetic structure.

19. A method of detecting a virus, comprising:

providing the device of claim 17;

causing a radio frequency to contact the device;

generating a magnetic field;

taking a first magnetic resonance measurement;

causing the device to contact a fluid;

taking a second magnetic resonance measurement after the device is in contact with the fluid; and detecting a change in the magnetic field between the first magnetic resonance measurement and the second magnetic resonance measurement.

* * * * *